(12) United States Patent
Takiguchi et al.

(10) Patent No.: US 6,869,933 B2
(45) Date of Patent: Mar. 22, 2005

(54) HIV-SPECIFIC CTL INDUCING PEPTIDES AND MEDICAMENTS FOR PREVENTING OR TREATING AIDS COMPRISING THE PEPTIDES

(75) Inventors: Masafumi Takiguchi, Tokyo (JP); Kiyoshi Miwa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 75 days.

(21) Appl. No.: 09/994,617

(22) Filed: Nov. 28, 2001

(65) Prior Publication Data

US 2003/0114369 A1 Jun. 19, 2003

Related U.S. Application Data

(63) Continuation of application No. PCT/JP00/03455, filed on May 29, 2000.

(30) Foreign Application Priority Data

May 28, 1999 (JP) ............................................. 11-149589

(51) Int. Cl.[7] .............................................. A61K 38/00
(52) U.S. Cl. ................................. 514/16; 435/5; 435/6; 435/91.2; 536/23.1; 536/23.72
(58) Field of Search ............................. 514/16; 435/5, 435/6, 91.2; 536/23.1, 23.72

(56) References Cited

U.S. PATENT DOCUMENTS

5,756,666 A 5/1998 Takiguchi et al.
6,037,135 A * 3/2000 Kubo et al. ................ 435/7.24

FOREIGN PATENT DOCUMENTS

WO 95/11255 4/1995
WO WO 00/26416 * 5/2000 ............ C12Q/1/70

OTHER PUBLICATIONS

Wilson C.C., et al. "Frequent detection of escape from cytotoxic T–lymphocyte recognition in perinatal human immunodeficiency virus (HIV) type 1 transmission: the ariel project for the prevention of transmission of HIV from mother to infant", Journal of Virology (May 1999), vol. 73, No. 5, pp. 3975–3985.

Lole K.S., et al. "Fill–length human immunodeficiency virus type 1 genomes from subtype C–infected seroconverters in India, with evidence of intersubtype recombination", Journal of Virology (Jan. 1999), vol. 73, No. 1, pp. 152–160.

Borrow P., et al. "Antiviral pressure exerted by HIV–1–specific cytotoxic T lymphocytes during primary infection demonstrated by rapid selection of CTL escape virus", Nature Medicine (1997), vol. 3, No. 2, pp. 205–211.

Couillin I, et al., "Impared cytotoxic T lymphocyte recognition due to genetic variations in the main immunogenic region of the human immunodeficiency virus 1 NEF protein", J. Exp. Med. (1994), vol. 180, No. 3, pp. 1129–1134.

* cited by examiner

*Primary Examiner*—Christopher Tate
*Assistant Examiner*—Roy Teller
(74) *Attorney, Agent, or Firm*—Oblon, Spivak, McClelland, Maier & Neustadt, P.C.

(57) ABSTRACT

Peptides which can induce specific CTLs for HIV, DNAs encoding for the peptides and medicaments for preventing and/or treating HIV comprising the peptides are provided. According to the present invention, peptides carrying novel CTL epitopes derived from HIV Pol or Env proteins are provided. These peptides can bind to HLA-A11, particularly HLA-A*1101 which is frequently encountered in Japanese people and induce HIV-specific cytotoxic T cells.

7 Claims, 2 Drawing Sheets

FIG. 1

SF2-Pol424-9
(QIYAGIKVK)

FIG. 2

SF2-Pol424-9-27

FIG. 3(A)

KOG-SF2-ENV202-9-32
(E : T Ratio = 2 : 1)

Specific Lysis (%)

FIG. 3(B)

KOG-SF2-Env202-9-56
(E : T Ratio = 2 : 1)

Specific Lysis (%)

HIV-SPECIFIC CTL INDUCING PEPTIDES AND MEDICAMENTS FOR PREVENTING OR TREATING AIDS COMPRISING THE PEPTIDES

The present application is a Continuation of PCT/JP00/03455 filed May 29, 2000.

TECHNICAL FIELD OF THE INVENTION

The present invention relates to peptides having an amino acid sequences of the partial region of the protein from Human Immunodeficiency Virus (referred to as "HIV" hereinafter) and which can induce an immune response against HIV, and medicaments comprising the peptide(s) for preventing and/or treating AIDS.

BACKGROUND OF THE INVENTION

Acquired immunodeficiency syndrome (referred to as "AIDS" hereinafter) is the disease caused by the infection of HIV. The investigations for medicaments to treat this disease have been actively performed, and although medicaments such as azidothymidine (referred to as "AZT" hereinafter) and dideoxyinosine (referred to as "DDI" hereinafter) have been practically used, they have some problems in their effects or side effects. Thus, medicaments which can completely treat the diseases caused by HIV infection have not been found and there is no prospect of the findings. On the other hand, a vaccine as a tool for preventing HIV infection and suppressing AIDS onset, which enhances the immune resistance against HIV, has been expected as a critical key to control the global and rapid spread of the disease and has been widely investigated. To date, various types of vaccine have been investigated and some of them are undergoing the clinical test.

The vaccines which have been reported to date include:
i) Vaccines which utilizes inactivated or attenuated virus particles: The method may be considered wherein a gene responsible for HIV pathogenicity is mutated or deleted (Proc. Natl. Acad. Sci. USA, 84, 1434, 1987) or the approach wherein related viruses such as simian viruses which shares the antigenecity of HIV are used (Science, 232, 238, 1987), but it would be difficult to practically use them due to their potential risks.
ii) Subunit vaccines utilizing partial antigen proteins from the viral antigenic proteins: This is the approach wherein only a partial antigenic protein of the virus particle is produce, for example, by genetic recombinant procedures and used as an immunogen (Proc. Natl. Acad. Sci. USA, 84, 6924, (1987), Ann. Int. Med., 114,119, (1991), Nature, 355,728, 1992). This approach is widely attempted and there are many clinical test cases. However, there are many problems such as poor increase in the titer of the neutralizing antibody or the persistency of the titer of the antibody. Also, although it would be expected for this approach that it would be effective in enhancing the humoral immunity such as the production of antibodies, the effect of this approach alone would not be necessary expected considering the infection manner of HIV, because this approach would not lead to the activation of cellular immunity which can kill the infected cells.
iii) Recombinant live vaccines such as vaccinia virus or BCG: This is the approach wherein a partial gene sequence from HIV is introduced into the gene of vaccinia virus (Nature, 332,728, 1988) or BCG (Nature, 351, 479, 1991) which can propagate in human cells. Theoretically, the enhancing effect on cellular immunity would be expected but there are some problems, for example, in that at least previously produced recombinant live vaccines of vaccinia did not trigger sufficient immune response, or viruses such as vaccinia, which are usually harmless, have the possibility of severe infection (Lancet et al. 337, 1034, 1991).
iv) Anti-idiotype antibodies: This is the approach wherein an anti-idiotype antibody is used as the alternative to the virus antigen (Proc. Natl. Acad. Sci. USA, 89, 2546, 1992).
v) Synthetic peptide vaccines: Synthesized peptides are considered in this approach, wherein the sequences of the determinant region of neutralizing antibodies are chemically synthesized.

The above described vaccines are of the type of humoral immune enhancer which mainly induce the neutralizing antibodies, while it is believed that cytotoxic T cells (referred to as "CTLs" hereinafter) which can impair infected cells are more important in defending the infection than humoral immunity with neutralizing antibodies, considering that HIV spreads more easily through the cell fusion between infected cells and non-infected cells than through virus particles. Actually, there is a report where if the patients who had been exposed to the chance of HIV infection were investigated, HIV specific CTLs were detected (J Clin. Invest., 93, 1293, (1994), Nature, Med., 1, 59, 1995). There is also a report wherein HIV carrying a mutated CTL epitope can escape from the attack of CTLs (Nature Med., 3, 205, 1997) and the appearance of HIV carrying such mutated epitope is believed to be the cause of the onset of AIDS in patients chronically infected with HIV(Nature Med., 3, 212, 1997).

Antigens such as virus-derived proteins are endogenously processed in cells to short fragments and are presented on the cell surface as a bounded form with major histocompatibility complex (referred to as "MHC" hereinafter). CTL recognizes the epitope peptide presented by Class I MHC antigen expressed on the cell surface and attack the target cells. More specifically, CTL recognizes both of the processed antigen fragment bound to the groove of MHC molecule and a part of the MHC molecule on the target cell simultaneously and attack the cell carrying them. Thus, the antigen recognition of CTL intensively depends on MHC on the cell surface. Such antigen recognition is called MHC restriction. It is known that the epitope peptides which bind to a particular MHC Class I antigen and which are presented by the antigen have about nine amino acids in length and their amino acids sequences are defined by certain rules (motif) (Nature, 351, 290, 1991, Eur. J. Immunol., 22, 2453, 1992, Nature, 353, 326, 1991, Nature, 360, 434, 1992, Immunogenetics, 38, 161, 1993).

Based on these findings, the inventors of the present invention have been searching CTL peptides which specifically impair HIV-1 infected cells and have already defined the peptides which can bind to HLA-B35, HLA-B51 and HLA-A31 among human Class I antigens, human Class I leukocyte antigens (referred to as "HLA" hereinafter), and which can induce HIV-1 specific CTLs (WO 95/11255). These peptides induced HIV-1 specific CTLs, restricted by each HLA alloantigen type.

Since HLA genes are the genes having very high diversities, the peptides which bind to HLA Class I antigens have also high diversities, although they comply with certain rules. This suggests that the peptides which are effective in the prevention and/or treatment of HIV infection may possibly differ among individuals, ethnic populations and the like. Therefore, in the prevention and/or the treatment of HIV infection wherein such peptides are used, a set of peptides is desired which can induce other HLA-restricted CTLs besides the known peptide groups.

SUMMARY OF THE INVENTION

It is an object of the present invention to provide a peptide which can induce the HIV-1 specific CTL. In particular, it is an object of the present invention to provide a peptide which can induce HIV-1 specific HLA-A*1101 restricted CTL.

It is also an object of the present invention to provide a DNA coding for the above-described peptide. It is further the object of the present invention to provide a medicament for preventing and/or treating AIDS, comprising said peptide.

It is also an object of the present invention to provide a peptide useful for developing HIV-1 vaccine, especially developing the vaccine in Asia. The major difficulty in HIV vaccine development consist in that HIV can easily mutate and escape the host immunity. Thus, the vaccine which use only one epitope as the immunogen has a great possibility of losing its effectiveness with time. It is an object of the present invention to provide multiple epitope peptides that can be simultaneously used as effective immunogens.

The peptides according to the present invention can bind to HLA-A*1101 antigen and induce HLA-A*1101 restricted CTLs targeting HIV-1 infected cells. The DNAs according to the present invention encode for said peptides.

The inventors of the present invention have defined the peptides which can bind to HLA-B*3501, HLA-B*5101 and HLA-A*3101 Class I antigen (WO 95/11255), as previously mentioned. HLA is the molecule which has high diversities among ethnics or individuals, while the peptides of the present invention are characterized in that they are the peptides derived from HIV-1 Pol or Env protein and which can bind to HLA-A11 molecule frequently found in Asian people, especially in Japanese people (HLA-A*1101) (Clayton J, Lonjon C, Whittle D: Allele and haplotype frequencies for HLA loci in various ethnic group: HLA volume I Genetic diversity of HLA functional and medical implication: Charron D. Paris Ed. : EDK Medical and Scientific International Publisher; 1997;665–820).

The peptides according to the present invention or the peptides encoded by the DNAs according to the present invention are the fragments of HIV-1 Pol or Env protein, which contain any of the amino acid sequence of QIY-AGIKVK (SEQ ID NO: 1), SVITQACPK (SEQ ID NO: 2), QIIEELIKK (SEQ ID NO: 3), QIIEKLIEK (SEQ ID NO: 4), ACQGVGGPSHK(SEQ ID NO: 5), AFDLSFFLK (SEQ ID NO: 6) and ALDLSHFLK (SEQ ID NO: 7) and carry HLA-A*1101 binding motif, and which can actually induce HLA-A*1101 restricted CTLs against HIV-1 infected cells.

BRIEF DESCRIPTION OF DRAWINGS

FIG. 1 shows the degree of recognition of the HLA-A*1101 restricted HIV-1 specific CTL epitope by the CTL clones. Black characters represent C1R-A*1101 cell and white characters represent C1R cell. The data were obtained with effector:target=2:1. Two lines of CTL clones were used for each peptide, respectively. Black circle (●) and white circle (○) represent SF2-Pol424-9-27 CTL clone. Black triangle (▲) and white triangle (Δ) represent SF2-Pol424-9-34 CTL clone.

FIG. 2 shows the CTL activity for the target cells infected with the recombinant vaccinia virus expressing Pol protein of HIV-1. The bars with shilling mark represents the specific lysis percentage for C1R-A*1101 infected with recombinant vaccinia virus expressing Pol protein of HIV-1. The white bar represents the specific lysis percentage for C1R-A*1101 infected with wild type vaccinia virus.

FIG. 3 shows the CTL activity for the target cells infected with the recombinant vaccinia virus expressing Env protein of HIV-1. The bars in FIGS. 3A and 3B represent the specific cell lysis percentage for C1R-A*1101 infected with the vaccinia virus expressing Env protein, C1R-A*1101 infected with wild type vaccinia virus, C1R infected with vaccinia virus expressing Env protein, C1R infected with wild type vaccinia virus, C1R-A*1101 pulsed with SF2-Env202-9 and C1R pulsed with SF2-Env202-9, from the top to the bottom. The peptide concentration was $10^{-6}$M.

DETAILED DESCRIPTION OF THE INVENTION

The whole proteins of HIV are described, for example, in Nature Vol. 313, pp.277–283 (1985) or Proc. Natl., Acad. Sci. USA Vol. 83, 002209-2213 (1986). The peptides of the present invention are the fragments of HIV and, furthermore, they have HLA-A*1101 motif and actually bind to HLA. Exemplary HLA-A*1101 binding motif includes the peptides consisting of 8 to 12 amino acids wherein the second amino acid thereof is selected from Val, Ile, Thr, Leu, Tyr, Cys or Phe and the C-terminal amino acid is Lys. Such peptides may be synthesized using a peptide-synthesizer. The binding of the peptides of the present invention containing HLA-A*1101 binding motif may be confirm by using the cells expressing HLA-A*1101. C1R or RMA-S cells may be used as such cells.

According to the present invention, the synthesized peptides are confirmed for their ability to actually stimulate the patient's peripheral blood monocytes (PBLs) and induce cytotoxic T cells (CTLs). Using such a procedure, peptides having the amino acids sequences of QIYAGIKVK (SEQ ID NO: 1), SVITQACPK (SEQ ID NO: 2), QIIEELIKK (SEQ ID NO: 3), QIIEKLIEK (SEQ ID NO: 4), ACQGVGGP-SHK (SEQ ID NO: 5). AFDLSFFLK (SEQ ID NO: 6) and ALDLSHFLK (SEQ ID NO: 7) were obtained, which are the fragments of HIV-1 Pol protein. The peptides of the present invention may be prepared by synthesizing them with peptide-synthesizer or by expressing the DNAs encoding for the peptides having any of the amino acids sequences of SEQ ID NO: 1 to SEQ ID NO: 7 with appropriate host-vector systems. Since the codon usage may vary depending on the host cell used, the preferred codon usage may be selected for each cell. DNAs which can hybridize with such DNAs under the stringent condition, and which bind to HLA-A11 antigen and induce cytotoxic T cells targeting HIV infected cells, may be used also. The stringent condition as used herein means, for example, the condition wherein annealing at 20–25 ° C. below the melting temperature Tm ($Tm=81.5°$ C.$+\log_{10}[Na^+]+0.41(G+C$ content %)−(600/sequence length)) in 2×SSC (20×SSC: NaCl 75.3 g/Lm sodium citrate 8802 g/L, pH7.0), and washing at 12–20° C. below the Tm with salt concentration of 0.1×SSC, regarding to the temperature and the salt concentration.

The techniques of isolation of DNA fragments, construction of vectors, transformation using recombinant DNA technology, production of peptides and measurement of CTL activity are well known to those skilled in the art.

The peptide of the present invention is useful as a vaccine, because it can induce HIV-1 specific CTL functioning as the T cell epitope. As a vaccine, the peptide solution alone or the combination thereof with one or more physiologically acceptable adjuvants may be administrated with a syringe, or they may be administrated, for example, by aerosol, through dermal absorption from mucous membrane. The peptide may be administrated by a single dose or multiple doses with 0.1 mg–100 mg/dosage. Plural peptides may be used simultaneously, which may be effective in certain cases. The formulation is not particularly limited, and may be freeze-dried or granulated with an excipient such as sugar. There are no acute toxicity observed for thus prepared peptide formulations according to the present invention. Adjuvants which may be used and which can increase the immunogenicity of the vaccine include a composition from cells such as BCG cells, ISCOM extracted from QuillA developed by Morein et al. (Immunostimulating complex, Nature, 308, 457, 1984; Nature, 344, 873, 1990), a saponin system QS-21 (J. Immunol., 148, 1438, 1992), liposome (J. Immunol., 148, 1585, 1992), alminium hidroxyde (alum), KLH (keyhole limpet hemocyanin) J. Virol., 65, 489, 1991). Each of above indicated references and Science, 255, 333, (1992) describes that immune response such as CTL can be induced in vivo by using such methods.

By using the epitope peptides according to the present invention, the methods may be applicable wherein CTLs are effectively induced within the body of patients by administrating the cells from the patients or the cells carrying HLA Class I antigen of the same haplotype, which were previously exposed to the epitope peptide, into the vein of the patients, or wherein CTLs are induced and expanded in vitro by culturing the peripheral blood lymphocytes from patients in vitro with the peptide, followed by returning the cells to the patients. Therefore, CTLs obtained by culturing peripheral blood lymphocytes carrying HLA-A*1101 antigen in the presence of any of the peptides having the sequence according to SEQ ID NO: 1 to SEQ ID NO: 7 may be used as an AIDS vaccine.

In practice, the peptide of the present invention is added to $10^7$–$10^9$ peripheral blood lymphocytes of the patient and the lymphocytes are administrated into the vein of the patient after culturing for from a few hours to one day, or alternatively, after CTLs are induced by continuously culturing the lymphocytes in the medium supplemented with 50 U/ml of recombinant IL-2 and 1 µg/ml of the peptide for a few weeks, they are injected into the vein of the patient. The cells may be cultured by the methods well known to those skilled in the art, then the cultured cells are suspended, for example, in saline after the medium component is washed out, for example, by centrifugation. Such therapeutic methods using cell injection have been utilized as a cancer treatment, which are well known to those skilled in the art (New Ing. J. Med., 313, 4185, 1085; Science, 233, 1318, 1986).

Additionally, the identified CTL epitopes according to the present invention may be effectively employed in vaccinia viruses or BCG live recombinant vaccines. When the DNA encoding for the peptides comprising any of the amino acid sequence according to SEQ ID NO: 1 to SEQ ID NO: 7 is introduced into the genes for recombinant proteins which are intended to be expressed in the recombinant live vaccine, the peptide will be processed in cells to be presented by HLA-A*1101 antigen after being expressed as a part of the antigen protein. This will allow the induction of CTL which recognize the peptide. The methods for expressing foreign genes in recombinant BCG live vaccines are detailed in WO 88/06626. The recombinant BCG live vaccines are detailed in J. Exp. Med., 178, 197 (1993). The dose and the dosage methods may be employed according to the dose and methods for the conventional variolation or BCG vaccine. They do not differ from the conventional variolation or BCG vaccine in the acute toxicity and the like. However, vaccinia virus should be carefully used as a therapeutic vaccine, because there may be the risk of sever infection in the patients whose immunocompetence was reduced by the onset of AIDS. Regarding with BCG vaccine, such cases have not been reported yet. The possibility of inducing the immuneresponse including CTL in vivo by such methods is shown, for example, in Nature, 332, 728 (1988) and Nature, 351, 479 (1991).

EXAMPLES

Example 1

Preparation of HLA-A*1101 Expressing Cells

C1R cells expressing HLA-A*1101 (C1R-A*1101) and RMA-S cells expressing HLA-A*1101 (RMA-S-A*1101) were prepared as literally described (Tissue Antigens, 52, 501-509,1998). RMA-S cells and C1R cells are the mouse cell line and the human cell line, respectively, which are defective in the transporter molecule TAP (Transporter Associated Protein) (Nature, 346, 476, 1990). C1R and RMA-S cells were cultured in RPMI1640 medium supplemented with 10% FCS. C1R-A*1101 and RMS-S-A*1101 cells were cultured in RPM1640 medium containing 10% FCS and 0.15mg/ml Hygromycin B. Epstein-Barr virus transformed cell line Tm-EBV (HLA-A11/A24, B52/B52, Cw7/Cw*1202) was maintained in RPMI1640 supplemented with 10% FCS.

Unless otherwise indicated, cloning of genes, transfection of cells and the like are performed according to the general procedures in the filed of molecular biology (Sambrook, J. et al., Molecular Cloning: A Laboratory Manual 2nd ed. (1989), Ausbel, F. M. et al., Current protocols in molecular biology, John Wiley & Sons, Inc.).

Example 2
Estimation of HLA-A*1101 Binding Peptides Derived from HIV-1-SF2 Strain
2-1. Synthesis of Peptides Peptides were synthesized by using an automated multiple peptides synthesizer (Shimadzu Model PSSM-8, Shimadzu Co. Kyoto Japan) and were confirmed by mass spectrometry. The peptides with not less than 90% purity were used in the following Examples.
2-2. Biding Ability of the Peptides to HLA-A*1101 Molecule Biding ability of the HIV-1-derived peptides to HLA-A*1101 molecule was examined by the peptide stabilization assay as described in Tissue Antigens, 52, 501-509.

The peptide stabilization assay method is described hereinafter.

RMA-S and C1R cells are the mouse cell line and the human cell line, respectively, both of which are defective in transporter molecule TAP (Transporter Associated Protein). Therefore, they express MHC class I antigen on the cell surface at only low level when they are cultured at 37° C. However, they are known to express peptide-unbounded class I antigen on the cell surface at high level when they are cultured at a low temperature (26° C.) (Nature, 346, 476, 1990).

Similarly, RMA-S-A*1101 and C1R-A*1101 cells express HLA-A*1101 antigen on the cell surface when cultured at 26° C., but the expression is reduced when they are cultured at 37° C. Additionally, the expression level of HLA-A*1101 antigen on RMA-S-A*1101 cell or C1R-A*1101 cell previously cultured at 26° C. will be also reduced like the cells cultured at 37° C., by placing the cells at 37° C. for 3 hours. However, if the peptides are added externally to bind to peptide-unbounded HLA-A*1101, resulting peptide-bounded HLA-A*1101 antigen does not disappear and remains the expression at high level even at 37° C. This was used to determine the binding ability of peptide to HLA-A*1101 antigen. In practice, the binding of the peptide was determined by adding a synthetic peptide to RMA-S-A*1101 or C1R-A*1101 cells cultured at 26° C., placing the cells at 26° C. for 1 hour and subsequently at 37° C. for 3 hours and then determining the expression level of HLA-A*1101 on the cell surface using flow cytometry with the anti-HLA-A*1101 monoclonal antibody. Commercially available monoclonal antibodies being capable of recognizing HLA-A antigen were used for anti-HLA-A*1101 monoclonal antibodies, but especially TP25.99 antibody which was a gift from Dr. Soldano Ferrone or MB40.5 antibody (ATCC HB-116) was primarily used.

As a result, 61 of 92 peptides synthesized bound to HLA-A*1101 antigen molecule. HLA-A*1101 restricted CTL inducing activity was further investigated for these 61 peptides.

Example 3

Induction of CTL from HIV-1 Infected Patients Using HLA-A*1101 Binding Peptide and the Cytotoxic Activity of the CTL CTLs were induced from HIV-1 infected patients using HLA-A*1101 obtained in Example 2 and the cytotoxic activity was examined.

3-1. Induction of CTL

Peripheral blood monocytes were prepared from LA-A*1101HIV-1 carrying seropositive patients IU (HLA-A1/A24, B38/B51,Cw7/–) and KOG (HLA-A2/A11, B46/B54, C1/–). Peripheral blood monocytes were prepared according to the conventional Ficoll-Conray specific gravity centrifugal method ("New detection method of the function of lymphocytes", Junichi Yada, Michio Fujiwara ed., Chu-Gai Igaku Co., 1987; "Molecular Immunology I" of New Biochemical Experiments Course 12, Tokyo Kagaku Dojin, 1989). Namely, after collecting blood with heparin syringe, the blood was diluted with saline, layered on Ficoll-Paque separating solution (Pharmacia), followed by centrifugation at 400×g for 30 minutes. Lymphocytes from intermediate layer were recovered with a pipette and were used after washing. $2\times10^6$ lymphocytes per well were placed in 24-well culture plates and cultured in RPMI640 (containing 10% FCS) supplemented with recombinant human IL-2 and a synthetic peptide at the final concentration of 50 U/ml and $10^{-6}$M respectively. The half of the medium was exchanged every 2–3 day by RPMI640 culture medium supplemented with 50 U/ml of recombinant human IL-2.

3-2. Determination of Cytotoxic Activity of CTL Induced by Using HLA-A*1101 Binding Peptides (CTL assay)

Specific CTLs were induced by stimulating the bulk culture with PHA and then re-stimulating the culture by adding irradiated autologous lymphocytes ($1\times10^6$) and $10^{-6}$M of each HLA-A*1101 binding peptide every 1 week. After thus re-stimulating the lymphocyte cultures for 2–3 times, the CTL activity in each culture for HLA-A*1101 expressing TM-EBV transformed cells which had been previously pulsed with the corresponding peptide was determined. The CTL assay was performed as described thereinafter.

HLA-A*1101 expressing Tm-EBV transformed cells ($1\times10^5$) were incubated for 60 minutes at 37° C. with 100 µCi of $Na_2{}^{51}CrO_4$ in saline, and washed 3 times with RPMI1640 medium containing 10% FCS. 50 µl of the suspension of labeled target cells in culture medium was added to each well of the 96-well plate ($5\times10^3$ cells/well). To the cells 50 µl of the solution of each HLA-A*1101 binding peptide diluted to the concentration of $4\times10^{-6}$M-$4\times10^{-11}$M was added and the cells were placed in $CO_2$ incubator at 37° C. for 30 minutes. Then cultured peripheral blood cells from patients which had been previously stimulated with the same peptide were added as effector cells at the effector:target (E:T) ratio of 2:1 (suspended in 100 µl of medium), and the mixture was placed in a $CO_2$ incubator at 37° C. for 4 hours.

The half of the culture medium in each of the well was taken and $^{51}$Cr released from the target cells caused by the cytotoxic activity of the patient's cultured peripheral blood lymphocytes was determined using γ-counter. The cytotoxic activity of CTL clone to the target cell (specific relative lysis, that is, the relative percentage of specific cell lysis) was calculated by formula (I):

Specific relative lysis (%) =(measurement of each well−minimum release)/(maximum release−minimum release) ×100    (I)

wherein "minimum release" is the spontaneous release of $^{51}$Cr from target cells which is measured for the well containing only target cells and "maximum release" is the release of label measured when the target cells were disrupted by adding the surfactant Triton X-100.

Figure 1:
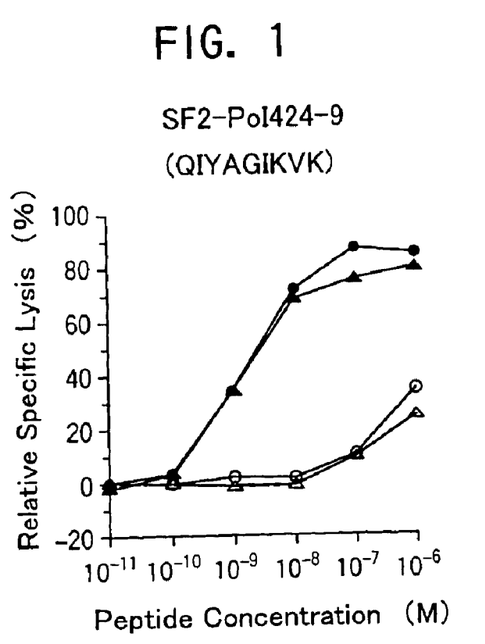
Figure 3A:
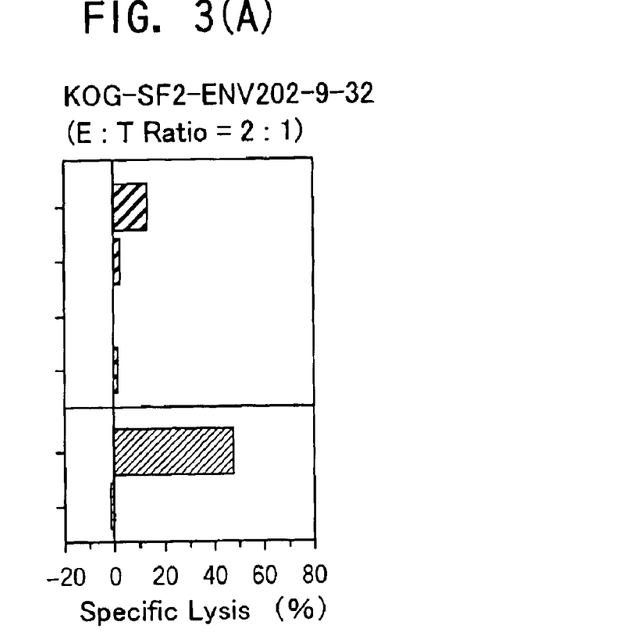
Figure 3B:
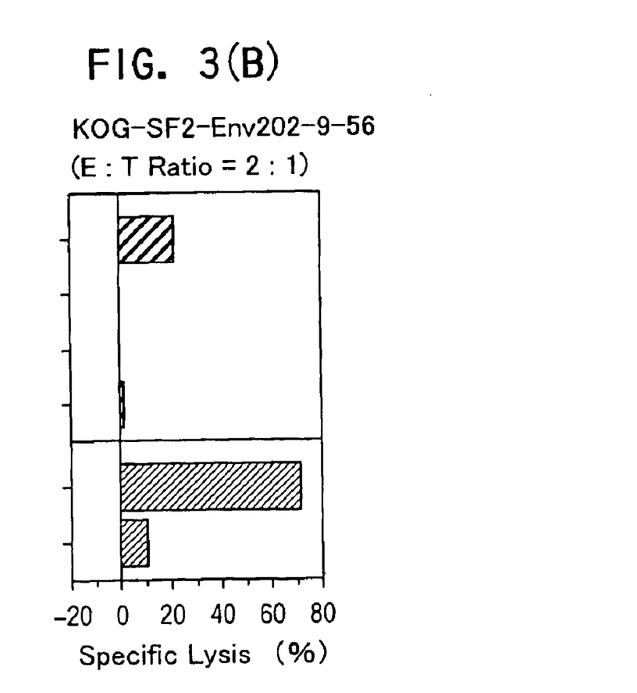

As a result, the new two peptides SF2-Pol 424-9 (SEQ ID NO: 1) and SF2-Env202-9 (SEQ ID NO: 2) were obtained from at least one of the two patients (FIG. 1 and 3).

Example 4

Identification of HLA-A*1101 Binding Peptides as CTL Epitopes

The two peptides SF2-Pol 424-9 (SEQ ID NO: 1) and SF2-Env202-9 (SEQ ID NO: 2) were confirmed to be the peptides which can actually be endogenously processed and presented by HLA-A*1101 molecule by using isolated specific CTL clones and vaccinia virus infected cells as target cells.

Firstly, the recombinant vaccinia virus carrying gag/pol gene or env gene from HV-1$_{SF-}$2 strain was generated as described in the reference (Virology, 175, 139, 1990). Cells were infected with the recombinant vaccinia virus by culturing them with 10 plaque-forming-units/cell of the recombinant virus or wilt type virus over night. Obtained cells should present endogenously processed HIV gene products on the cell surface in the HLA antigen-bounded form. On the other hand, CTL clones specific to the two peptides SF2-Pol 424-9 (SEQ ID NO: 1) and SF2-Env202-9 (SEQ ID NO: 2) were isolated from peptide-specific bulk cultures derived from HIV infected patients, respectively.

CTL assay was performed substantially as described in Example 3-2 using thus obtained vaccinia virus infected cell as target cells. Briefly, infected cells ($1\times10^5$) were incubated for 60 minutes with 100 µCi of $Na_2{}^{51}Cr_4$ in saline (at 26° C. for 90 minutes when C1R-A*1101 cell or RMA-S-A*1101 cell was used), and washed three times with RPMI1640 culture medium containing 10% FCS and used as labeled target cells. Labeled target cells ($5\times10^3$) were suspended in 50 µl of the culture medium and were added to each well of 96-well plates. To the cells 50 µl of the solution of each HLA-A*1101 binding peptide diluted to the concentration of $4\times10^{-6}$M–$4\times10^{-11}$M was added and the cells was placed in $CO_2$ incubator at 37° C. for 30 minutes. HIV-Pol or Env specific CTL clone isolated as previously described was added as effector cells at the effector:target (E:T) ratio of 1:1–4:1 (suspended in 100µl of medium), and the mixture was placed in a $CO_2$ incubator at 37° C. for 4 hours. Then, the half of the culture medium in each of the well was taken and $^{51}Cr$ release from the target cells caused by the cytotoxic activity of the patient's cultured peripheral blood lymphocytes was determined using γ-counter. Two lines of CTL were examined for each peptide and the cytotoxic activity of CTL clones to the target cells was calculated by the above-described formula (I).

restricted HIV-1 specific CTL epitopes. These cells were used as effector cells, and C1R-A*1101 and C1R cells previously pulsed with the corresponding peptide were used as target cells, to determine the CTL activity. The results are shown in Table 1A and 1B.

CTL activity specific for SF2-Pol424-9 and Pol496-505 was induced in one of six patients. On the other hand, CTL activity for Pol313-321 was induced in three patients. These results suggest that Pol epitopes are those among the major target molecules of HLA-A11 restricted CTL, although they may have individual differences

TABLE 1A

Induction of the specific CTL by a single stimulation with the peptides in PBL from HIV-seropositive patients carrying HLA-A11

| peptide | sequence | IU 40:1* | 5:1 | TAK 40:1 | 5:1 | KOG 40:1 | 5:1 |
|---|---|---|---|---|---|---|---|
| SF2-Pol424-9 | QIYAGIKVK (SEQ ID NO:1) | 27.4** | 11.7 | 2.3 | 2.0 | −0.2 | 3.1 |
| Pol496-505 | IYQEPFKNLK (SEQ ID NO:8) | 8.00 | 4.6 | 12.9 | 3.0 | −0.6 | −2.9 |
| Pol313-321 | AIFQSSMTK (SEQ ID NO:9) | 53.5 | 26.8 | 0.7 | 1.1 | 13.6 | 3.7 |
| Env77-85*** | DPNPQEVVL (SEQ ID NO:10) | 2.5 | 1.5 | 0.5 | 0.0 | 0.2 | −0.1 |

TABLE 1B

| peptide | sequence | SKG 40:1 | 5:1 | SSK 40:1 | 5:1 | SZK 40:1 | 5:1 |
|---|---|---|---|---|---|---|---|
| SF2-Pol424-9 | QIYAGIKVK (SEQ ID NO:1) | −3.7 | −1.7 | 7.0 | −3.3 | 4.9 | −0.2 |
| Pol496-505 | IYQEPFKNLK (SEQ ID NO:8) | 4.9 | −2.8 | 5.1 | 3.2 | 2.5 | 2.6 |
| Pol313-321 | AIFQSSMTK (SEQ ID NO:9) | 2.8 | −3.7 | −2.4 | 2.3 | 31.1 | 8.2 |
| Env77-85*** | DPNPQEVVL (SEQ ID NO:10) | 1.7 | −3.6 | −0.3 | −2.8 | −1.1 | −0.4 |

Figure 2:
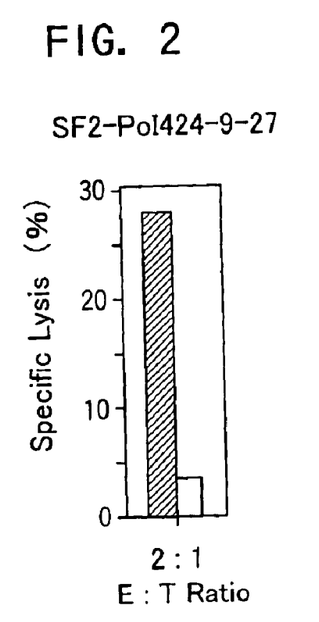

*effector: target ratio
**relative cell lysis(%):relative cell lysis ratio (%) as lysis of HLA-A*1101 positive Tm EBV transformed cells pulsed with the peptide (1 µM) minus the lysis of the cells in the absence of the peptide ].
***negative control peptide All the CTL clones exhibited the cytotoxic activity to C1R-A*1101 which had been pulsed with the corresponding peptide (FIG. 1 and 3, effector: target=2:1). On the other hand, these CTL clones could kill C1R-A*1101 cells which were infected with vaccinia virus expressing HIV-1 Pol protein or Env protein at various effector: target ratio, while they did not kill cells infected with wild type vaccinia virus (FIGS. 2 and 3). These results indicate that the two peptides SF2-Pol 424-9 and SF2-Env202-9 contain HLA-A*1101 restricted HIV-1 specific CTL epitopes.

Example 5

Generality of each Epitopes in HIV-1 Infected Patients and Comparison of the Ability of Inducing Specific CTL between Each Epitopes To investigate whether the epitope SF2-Pol424-9 (SEQ ID NO: 1) of the present invention and two known epitopes were generally and intensively presented in HIV-1 infected patients carrying HLA-A*1101, peripheral blood monocytes (PBMCs) from six HIV-1 seropositive patients carrying HLA-A*1101 were cultured for one week with the peptide of the present invention and Pol313-321 (AIFQSSMTK) (SEQ ID NO;9(J. Immunol 159, 1648–1657,197) and Pol496-505 (HIV Sequence Database, Los Alamos National Laboratory, Los Alamos, 1997) known to be HLA-A*1101

Example 6

The Ability of Peptides Derived from HIV-1 Subtype E and HIV-1 Subtype B in Inducing Specific CTLs Using similar procedures, epitope peptides derived from HIV-1 subtype E and HIV-1 subtype B were searched to select Pol 675-9-5E (QIIEELIKK) (SEQ ID NO:3), Pol 675-9-5K8E (QIIEKLIEK) (SEQ ID NO: 4), Gag 349-11 (ACQGVGGPSHK) (SEQ ID NO: 5), Nef 84-9-2F6F (AFDLSFFLK) (SEQ ID NO: 6) from subtype E and Nef 84-9-2L (ALDLSHFLK) (SEQ ID NO: 7) from subtype B as epitope candidates. Then, human peripheral blood monocytes infected with HIV-1 subtype E or subtype B were individually cultured with these peptides respectively for one week and CTL activity was determined by using these cells as effector cells and HLA-A*1101 positive EBV-transformed cells as target cells. The results are shown in Table 3A, 3B and Table 4.

Pol 675-9-5E could induce the specific CTL from five of seven patients, Pol 675-9-5K8E could induce the specific CTL from two of six, Nef 84-9-2F6F could induce the specific CTL from six of seven, Gag 349-11-9S could induce the specific CTL from three of seven and Nef 84-9-2L could induce the specific CTL from three of five patients. Peptides from subtype E could not be recognized by corresponding subtype B specific CTLs, and also peptides subtype E specific CTLs did not recognize subtype B peptides. This indicated that these peptides are subtype E specific epitopes. Additionally, among five patients who were HLA-A11 positive and infected with HIV-1 subtype B, there was one patient in whom the specific CTL could be induced by Nef 84-9 (AVDLSHFLK) (SEQ ID NO; 11) (J. Immunol 146: 1560–1565, 1991) but not by Nef 84-9-2L. To the contrary, there was also one patient in whom specific CTL could be induced by Nef 84-9-2L but not by Nef 84-9 (Table 4). This makes one to believe that Nef 84-9-2L is the epitope distinct from Nef 84-9.

TABLE 3A

Induction of the specific CTL after a single stimulation with the peptides in peripheral blood monocytes (PBLMC) from HIV-subtype E-seropositive patients carrying HLA-A11

| | | HIV-1 infected patient | | | |
|---|---|---|---|---|---|
| peptide | sequence | TT-005 | TT-007 | TT-008 | TT-009 |
| Pol 675-9-5E | QIIEELIKK (SEQ ID NO:3) | 3.4* | 55.1 | 23.4 | 63.8 |
| Pol 675-9-5K8E | QIIEKLIEK (SEQ ID NO:4) | −4.1 | 21.7 | 10.3 | 4.5 |
| Nef 84-9-2F6F | AFDLSFFLK (SEQ ID NO:6) | −1.3 | 24.6 | 75.5 | 76.5 |
| Gag 349-11-9S | ACQGVGGPSHK (SEQ ID NO:5) | 4.0 | 84.3 | 82.9 | 40.4 |

TABLE 3B

Continued from table 3A

| | | HIV-1 infected patient | | |
|---|---|---|---|---|
| peptides | sequence | TU-002 | TU-003 | TU-007 |
| Pol 675-9-5E | QIIEELIKK (SEQ ID NO:3) | 3.4 | 0.2 | 5.7 |
| Pol 675-9-5K8E | QIIEKLIEK (SEQ ID NO:4) | 5.6 | −5.6 | — |
| Nef 84-9-2F6F | AFDLSFFLK (SEQ ID NO:6) | 15.4 | 41.2 | 64.2 |
| Gag 349-11-9S | ACQGVGGPSHK (SEQ ID NO:5) | 3.9 | −2.8 | 3.4 |

*relative cell lysis (%):relative cell lysis ratio (%) as lysis of HLA-A*1101 positive Tm EBV transformed cells pulsed with the peptide (1 μM) minus the lysis of the cells in the absence of the peptide; effector:target cell ratio was 40:1

TABLE 4

Induction of the specific CTL after a single stimulation with the peptides in peripheral blood monocytes (PBLMC) from HIV-subtype B-seropositive patients carrying HLA-A11

| | | HIV-1 infected patient | | | | |
|---|---|---|---|---|---|---|
| peptide | sequence | KI-005 | KI-015 | KI-035 | KI-030 | KI-036 |
| Nef 84-9 | AVDLSHFLK (SEQ ID NO: 11) | 25.3* | 68.6 | 5.8 | 6.6 | 16.5 |
| Nef 84-9-2L | ALDLSHFLK (SEQ ID NO:7) | 68.3 | 6.3 | 16.4 | 5.5 | 50.4 |

*relative cell lysis (%):relative cell lysis ratio (%) as lysis of HLA-A*1101 positive Tm EBV transformed cells pulsed with the peptide (1 μM) minus the lysis of the cells in the absence of the peptide; effector:target cell ratio was 40:1

According to the present invention, novel seven epitopes of HIV-1 protein and a powerful tool for development of vaccines which can induce HLA-A11 restricted CTLs are provided. The peptides according to the present invention can induce HIV-1 protein specific HLA-A11 restricted CTLs. Since HLA-A11 is frequently encountered in Asian people, particularly in Japanese people, the peptides of the present invention provide the very important tools for the basis of AIDS investigation in Asia and for the development of HIV-1 vaccines.

What is claimed is:

1. An isolated DNA molecule coding for a peptide having an amino acid sequence.

2. The DNA molecule of claim 1, wherein the codon usage of the DNA molecule is optimized for the cell used for expression of said DNA molecule.

3. A host cell comprising the DNA molecule of claim 2.

4. A host cell comprising the DNA molecule of claim 1.

5. An expression vector comprising the DNA molecule of claim 1.

6. A method of inducing cytotoxic CTL targeting to a HIV infected cell comprising:

expressing the DNA molecule of claim 1 in a host cell to produce a peptide of SEQ ID NO: 4;

obtaining said peptide of SEQ ID NO: 4;

administering said peptide of SEQ ID NO: 4 to a subject in need thereof.

7. The method of claim 6, wherein said administering comprises a method selected from the group consisting of injection, aerosol, and transdermal application.

* * * * *

UNITED STATES PATENT AND TRADEMARK OFFICE
CERTIFICATE OF CORRECTION

PATENT NO.    : 6,869,933 B2                              Page 1 of 1
DATED         : March 22, 2005
INVENTOR(S)   : Masafumi Takiguchi et al.

It is certified that error appears in the above-identified patent and that said Letters Patent is hereby corrected as shown below:

<u>Column 15,</u>
Line 29, "An isolated DNA molecule coding for a peptide having an amino acid sequence." should read -- An isolated DNA molecule coding for a peptide having an amino acid sequnce of SEQ ID NO: 4 --

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 9
<212> TYPE: PRT
<213> ORGANISM: Human immunodeficiency virus type 1

<400> SEQUENCE: 1

Gln Ile Tyr Ala Gly Ile Lys Val Lys
1               5

<210> SEQ ID NO 2
<211> LENGTH: 9
<212> TYPE: PRT
<213> ORGANISM: Human immunodeficiency virus type 1

-continued

```
<400> SEQUENCE: 2

Ser Val Ile Thr Gln Ala Cys Pro Lys
1               5

<210> SEQ ID NO 3
<211> LENGTH: 9
<212> TYPE: PRT
<213> ORGANISM: Human immunodeficiency virus type 1

<400> SEQUENCE: 3

Gln Ile Ile Glu Glu Leu Ile Lys Lys
1               5

<210> SEQ ID NO 4
<211> LENGTH: 9
<212> TYPE: PRT
<213> ORGANISM: Human immunodeficiency virus type 1

<400> SEQUENCE: 4

Gln Ile Ile Glu Lys Leu Ile Glu Lys
1               5

<210> SEQ ID NO 5
<211> LENGTH: 11
<212> TYPE: PRT
<213> ORGANISM: Human immunodeficiency virus type 1

<400> SEQUENCE: 5

Ala Cys Gln Gly Val Gly Gly Pro Ser His Lys
1               5                   10

<210> SEQ ID NO 6
<211> LENGTH: 9
<212> TYPE: PRT
<213> ORGANISM: Human immunodeficiency virus type 1

<400> SEQUENCE: 6

Ala Phe Asp Leu Ser Phe Phe Leu Lys
1               5

<210> SEQ ID NO 7
<211> LENGTH: 9
<212> TYPE: PRT
<213> ORGANISM: Human immunodeficiency virus type 1

<400> SEQUENCE: 7

Ala Leu Asp Leu Ser His Phe Leu Lys
1               5

<210> SEQ ID NO 8
<211> LENGTH: 10
<212> TYPE: PRT
<213> ORGANISM: Human immunodeficiency virus type 1

<400> SEQUENCE: 8

Ile Tyr Gln Glu Pro Phe Lys Asn Leu Lys
1               5                   10

<210> SEQ ID NO 9
<211> LENGTH: 9
<212> TYPE: PRT
<213> ORGANISM: Human immunodeficiency virus type 1
```

```
<400> SEQUENCE: 9

Ala Ile Phe Gln Ser Ser Met Thr Lys
1               5

<210> SEQ ID NO 10
<211> LENGTH: 9
<212> TYPE: PRT
<213> ORGANISM: Human immunodeficiency virus type 1

<400> SEQUENCE: 10

Asp Pro Asn Pro Gln Glu Val Val Leu
1               5

<210> SEQ ID NO 11
<211> LENGTH: 9
<212> TYPE: PRT
<213> ORGANISM: Human immunodeficiency virus type 1

<400> SEQUENCE: 11

Ala Val Asp Leu Ser His Phe Leu Lys
1               5
```